United States Patent
Nopp et al.

(10) Patent No.: US 8,954,159 B2
(45) Date of Patent: Feb. 10, 2015

(54) ACCELERATED FITTING OF EAR IMPLANTS

(71) Applicant: MED-EL Elektromedizinische Geraete GmbH, Innsbruck (AT)

(72) Inventors: Peter Nopp, Axams (AT); Chris Durst, Nottingham (GB)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 210 days.

(21) Appl. No.: 13/623,917

(22) Filed: Sep. 21, 2012

(65) Prior Publication Data

US 2013/0079845 A1  Mar. 28, 2013

Related U.S. Application Data

(60) Provisional application No. 61/538,274, filed on Sep. 23, 2011.

(51) Int. Cl.
*A61N 1/00* (2006.01)
*A61N 1/36* (2006.01)

(52) U.S. Cl.
CPC ................... *A61N 1/36032* (2013.01)
USPC .............................. 607/57; 607/55

(58) Field of Classification Search
CPC ................... A61N 1/0541; A61N 1/36032
USPC ...................................... 607/55, 57
See application file for complete search history.

(56) References Cited

U.S. PATENT DOCUMENTS

2010/0152813 A1* 6/2010 Lineaweaver et al. .......... 607/57

* cited by examiner

*Primary Examiner* — Niketa Patel
*Assistant Examiner* — William Levicky
(74) *Attorney, Agent, or Firm* — Sunstein Kann Murphy & Timbers LLP

(57) ABSTRACT

Fitting a multi-channel cochlear implant system to an implanted patient is described. A fit map database is accessed that contains parameter data from fit maps of previously measured cochlear implant patients. For subsets of signal channels in each fit map, an average deviation is established between estimated parameter values and measured parameter values across signal channels not in a given subset based on measured parameter values of signal channels in the given subset. For a given number of signal channels, a subset of the same number of signal channels is identified that has a minimum average deviation. Then fit parameters for signal channels in the identified subset are measured and fit parameters for the remaining signal channels not in the identified subset are estimated.

23 Claims, 3 Drawing Sheets

ACCELERATED FITTING OF EAR IMPLANTS

This application claims priority from U.S. Provisional Patent Application 61/538,274, filed Sep. 23, 2011, which is incorporated herein by reference.

TECHNICAL FIELD

The present invention relates to ear implants, and more specifically to custom fitting of ear implant systems such as cochlear implants.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108 by external transmitter coil 107. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

To allow optimal performance, an ear implant system such as a cochlear implant needs to be adapted for the individual user. This adaptation process is normally referred to as the fitting process, or simply fitting. During the fitting process, several parameters within the cochlear implant system are set to best match the needs of the individual user. The result of this fitting process is normally referred to as a fitting or a map. One example of such a parameter is the Maximum Comfortable Loudness (MCL) level, i.e. the charge or stimulation level which produces a hearing impression which is comfortably loud but just without being too loud. Another example is Threshold (THR) level, which is the charge or stimulation level which produces a just audible, or alternatively a just-inaudible, hearing sensation. Other possible parameters concern, for example, the frequency distribution across the channels of the cochlear implant, or the loudness growth curve (commonly referred to as the maplaw). Among these parameters, the MCL is the one which invariably needs to be fitted to the each cochlear implant user individually, whereas for the other parameters reliable default values exist in general Several methods are used to obtain the necessary fitting parameters. For example, psychoacoustic methods as well as objective measures are used to obtain MCL and THR levels. In psychoacoustic methods, the cochlear implant user is asked to indicate which stimulation level produces a hearing sensation of the desired loudness (e.g. maximum comfortably loud for MCL or just not audible for THR). In objective measures, it is attempted to derive these levels from evoked potential or objective response measurements. One possible objective response used in this context is the threshold at which the stapedial reflex occurs, also called the electrical stapedial reflex threshold (ESRT). The ESRT is well correlated with MCL levels and can thus be used to determine MCL levels. Other objective measures concern evoked potentials measured along the cochlear pathway, from peripheral responses measured inside the cochlea to responses from the brainstem to responses from the auditory cortex, for example, measurements of electrically evoked compound action potential (ECAP) and/or electrically evoked auditory brain stem response (EABR).

Whatever method is used, the fitting of a cochlear implant is a relatively time-consuming procedure. Ideally, all channels in an implant need to be assessed individually to obtain the necessary parameters, which can require attention and cooperation by the implant user for a relatively long period of time. Thus, in children and other individuals with a restricted attention span or lesser ability to comply with the measurement paradigm, this procedure presents a serious challenge to both the clinician and the patient. Therefore, procedures allowing accelerated fitting are desirable.

Several methods are known for accelerating the fitting process in cochlear implants. One method concerns the use of interpolation. Necessary channel-specific parameters are obtained using psychoacoustics or objective measures for only a subset of the available channels in a cochlear implant, and the parameters on the remaining channels are estimated using those obtained parameters. For example, MCL levels may be obtained just for odd-number channels in the cochlear implant (i.e. channels 1, 3, 5 etc.) using any of the known methods, and MCL levels for the even-number channels are determined by interpolation. In many cases, this may be a linear interpolation where parameters for unmeasured channels in between measured channels are derived by linear interpolation. However, any other method of interpolation, or in more general terms, any other method of deriving estimated parameter values from measured parameters values can be used as well. In such endeavors, the question remains on which channels should parameters be obtained using psychoacoustics or objective measures, and on which channels should parameters be estimated based on the previously obtained parameters. To date, no method exists to guide the clinician in selecting the most appropriate channels for measuring or estimating these fitting parameters.

SUMMARY

Embodiments of the present invention are directed to a procedure for accelerated fitting of a multi-channel cochlear implant system to an implanted patient. A fit map database is accessed that contains fully measured (i.e. not estimated) parameter data from fit maps of previously measured cochlear implant patients. For subsets of signal channels in each fit map, an average deviation is established between estimated parameter values and measured parameter values across signal channels not in a given subset based on measured parameter values of signal channels in the given subset. For a given number of signal channels, a subset of the same number of signal channels is identified that has a minimum average deviation. Then fit parameters for signal channels in the identified subset are measured and fit parameters for the remaining signal channels not in the identified subset are estimated.

The method may further include increasing the given number of signal channels and repeating the identifying, measuring and estimating steps. For example, the initial given number of signal channels may be one, and the increasing step may be performed multiple times as determined by a clinician fitting the implanted patient or by fit software using the method. A clinician fitting the implanted patient or fit software using the method may also determine the given number of channels. Identifying the subset of signal channels with the minimum average deviation may include identifying an order in which to measure the signal channels in the identified subset.

Measuring fit parameters may include using psychoacoustic and/or objective measurements. For example, psychoacoustic measurements may be used to determine an MCL stimulation level and/or a THR stimulation level. Objective measurements may include measuring an electrically evoked compound action potential (ECAP), an electrical stapedius reflex threshold (ESRT), and/or an electrically evoked auditory brain stem response (EABR) which can be used to determine MCL and/or THR levels. Estimating fit parameters may include using linear interpolation.

Embodiments also include a cochlear implant fit to an implanted patient using a method according to any of the above, and a computer program product implemented in a computer readable storage medium for fitting an implanted electrode of a cochlear implant to an implanted patient and including program code for performing a method according to any of the above.

DETAILED DESCRIPTION

Embodiments of the present invention are directed to a process for accelerated fitting of a multi-channel cochlear implant system to an implanted patient which identifies those signal channels on which fitting parameters should be measured using psychoacoustics or objective measures, and those signal channels on which fitting parameters should be estimated. This provides more rapid and more targeted fitting and enables clinicians to avoid using inappropriate channel subsets when time does not allow all channels in a map to be assessed using psychoacoustics or objective measures.

Figure 1:
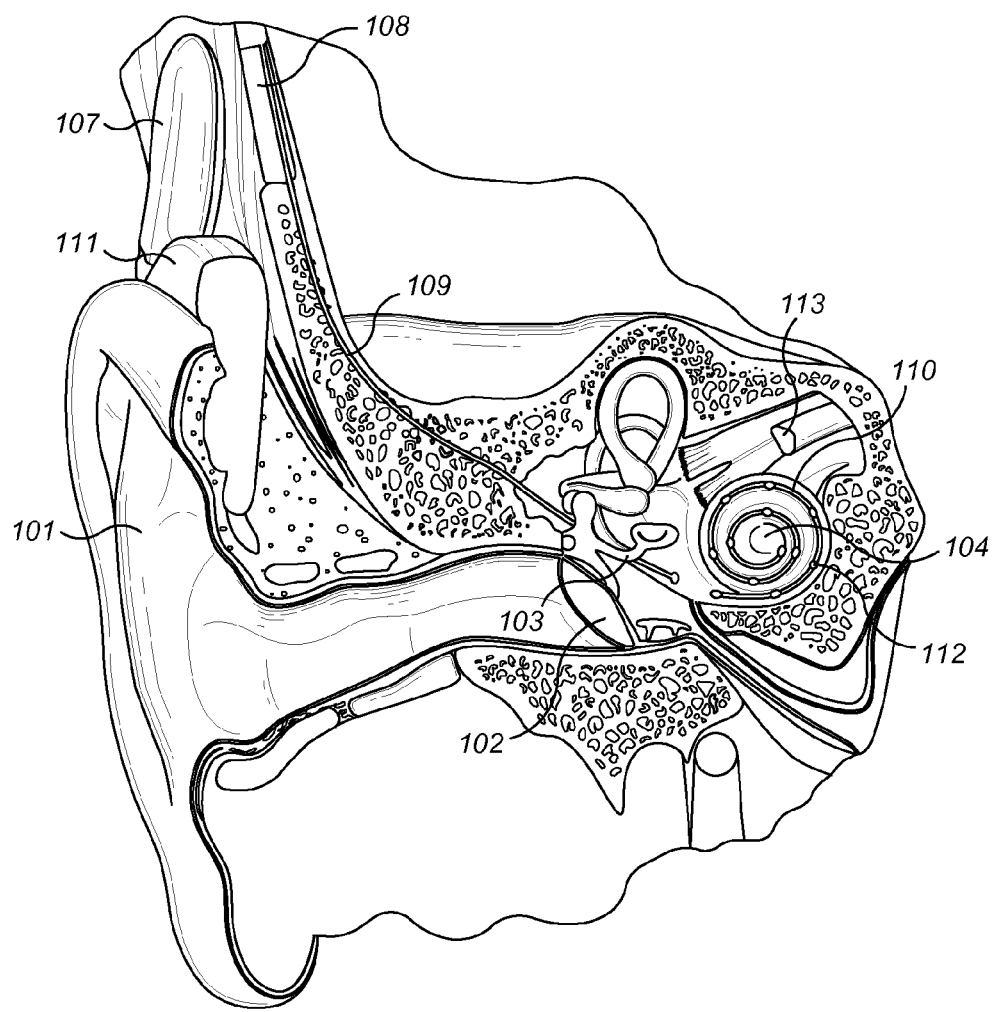
FIG. 1 shows anatomical structures in a human ear having a cochlear implant system.
Figure 2:
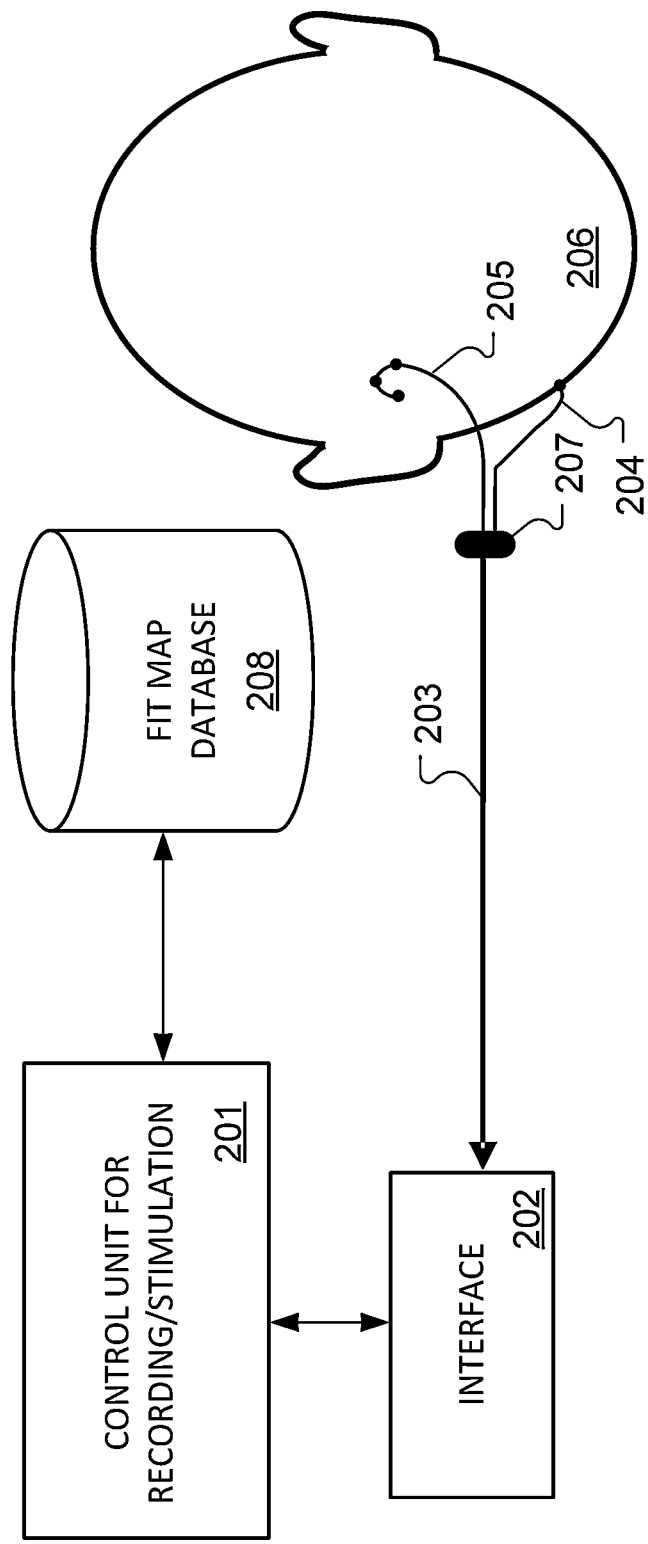
FIG. 2 shows a block diagram of a cochlear implant fitting system according to one specific embodiment of the present invention.

FIG. 2 shows a block diagram of a cochlear implant fitting system according to one specific embodiment of the present invention. Control unit 201 for recording and stimulation, for example, a Med-El Maestro CI system, generates stimulation signals and analyzes objective measurement responses. Connected to the control unit 201 is an interface box 202, for example, a diagnostic interface system such as the DIB II conventionally used with the Maestro CI system that formats and distributes the input and output signals between the control unit 201 and the system components implanted in the patient 206. For example, as shown in FIG. 2, there may be an interface lead 203 connected at one end to the interface box 202 and at the other end having electrode plug 207 that then divides into a cochlear implant electrode 204 and an extra-cochlear ground electrode 205. After delivering a stimulation pulse, a cochlear implant electrode 204 may be used as a sensing element to determine current and voltage characteristics of the adjacent tissue, i.e., obtain the objective response data such as ESRT, ECAP and/or EABR data which can be used to determine MCL and/or THR levels. For psychoacoustic measurements, a clinician or fit software may use the control unit 201 to deliver test stimulation signals to the patient to identify MCL and/or THR levels. Control unit 201 also has access to a fit map database 208 that contains parameter data from fit maps of previously measured implant patients as described below.

Figure 3:
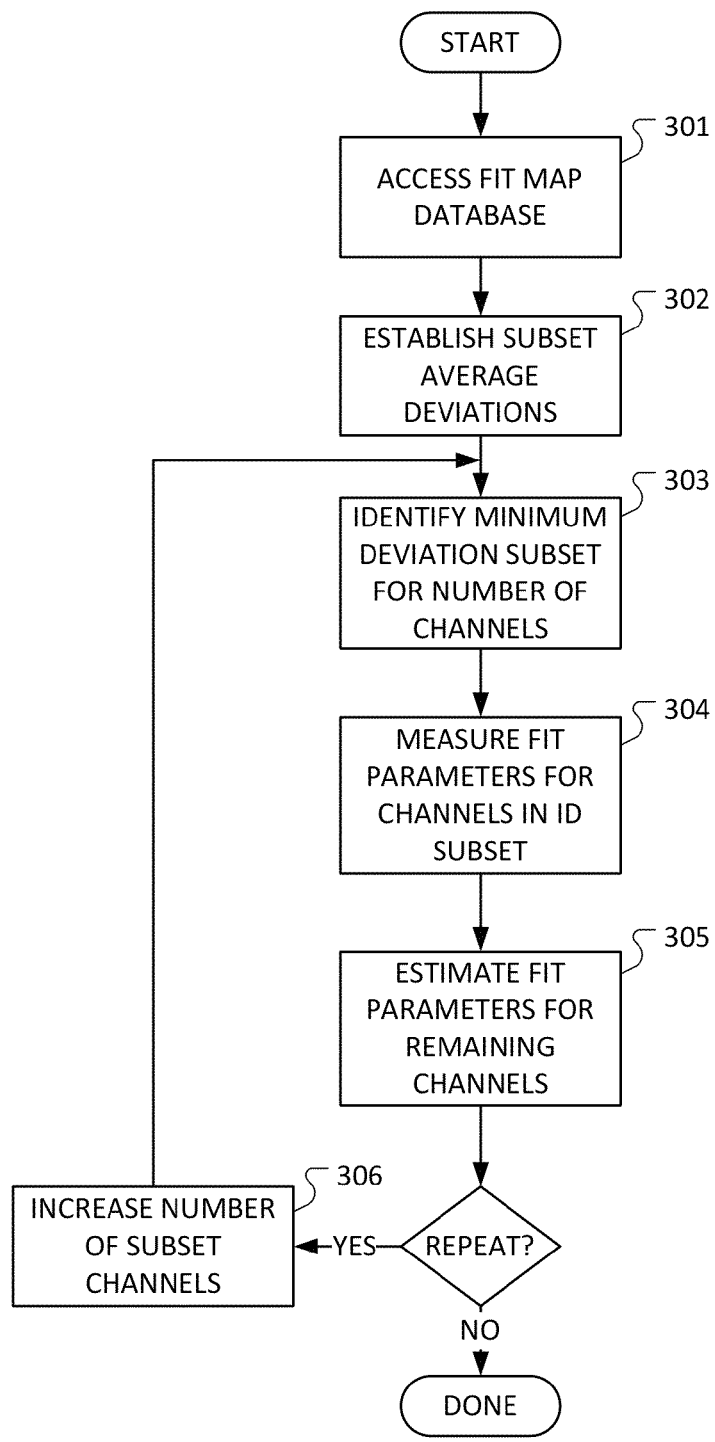
FIG. 3 shows various steps in a channel fitting process according to an embodiment of the present invention.

FIG. 3 shows various logical steps in an algorithm for determining cochlear implant fitting parameters using a system such as the one shown in FIG. 2. First, the method accesses the fit map database that contains parameter data from fit maps of previously measured cochlear implant patients, step 301. For subsets of signal channels in each fit map, an average deviation is established between estimated parameter values and measured parameter values across signal channels not in a given subset based on measured parameter values of signal channels in the given subset, step 302. Then, for a given number of signal channels, a subset of the same number of signal channels is identified that has a minimum average deviation step 303. The given number of channels may be determined by a clinician fitting the implanted patient or by fit software using the method. Identifying the subset of signal channels with the minimum average deviation, step 303, may include identifying an order in which to measure the signal channels in the identified subset. From that, fit parameters for signal channels in the identified subset are measured, step 304, and fit parameters for the remaining signal channels not in the identified subset are estimated, step 305.

Optionally, the method may further include increasing the given number of signal channels, step 306, and repeating the identifying, measuring and estimating steps, 303-305. For example, the initial given number of signal channels may be one, and the increasing step 306 may be performed multiple times as determined by a clinician fitting the implanted patient or by fit software using the method.

For example, assume that the channel subset in step 303 includes all odd-number signal channels and linear interpolation is used for the estimated signal channels in step 305. Then, the average deviation would be calculated in step 302 by averaging the deviation between measured values and estimated values across all even-number signal channels. For determining the global average deviation, for each subset the per-map average deviations can be averaged across all fitting maps. For the remaining analysis, subsets of channels can be organised by size, i.e. the number of channels included in the subset. Then, for each size, step 303 can identify that subset which yields the smallest global average deviation, i.e., the minimum deviation subset.

For each size subset, an optimum subset can be identified which contains those signal channels for which fitting parameters are preferably measured using psychoacoustics or objective measures, and correspondingly, on the remaining channels (i.e. the channels not included in the subset) fitting parameters are preferably estimated. The result of this analysis can then be used to guide the clinician in selecting the appropriate channels for a certain subset size. For example, in the fitting software, the clinician may be asked how many channels he would like to assess using psychoacoustics or an objective measure, and the software would then suggest the optimum subset based on the analysis as described above.

The fit map database can be any collection of maps considered appropriate for this purpose. For example, the fit map database could be compiled to be representative for fit maps on a world-wide or nation-wide basis, or to just be representative of a particular clinic, a particular patient age group, gender, or diagnosis, etc. The data in the fit map database, however, should correspond to the measure intended to be used on the signal channels included in the subset. For example, if ESRT is to be used to obtain fitting parameters on those signal channels included in the subset, then the fit map database should contain ESRT data or other data corresponding to ESRT data.

Embodiments of the present invention also can be used for a more flexible approach in which the clinician does not need to or cannot a priori fix the size of the subset. Accordingly the recommended signal channel subsets should be compatible with recommended subsets of smaller size such that new measurements can be added to already obtained measurements while still minimizing expected interpolation errors. For example, the fitting software may offer the clinician a recommendation for the most beneficial initial signal channel (or a range of signal channels in a case of likely equal performance) to measure as the basis for estimation from an initial subset size of one. Once this initial fitting measure is complete, and if further measures are desirable and possible, then a recommendation can be made for the next signal channel (or range of signal channels) to measure as the basis for estimation from a subset size of two. The process can iterate until the clinician decides that no further measurements can/should be carried out. In this way, at whatever size subset that the clinician decided to stop using psychoacoustics and/or objective measures and uses estimation for the remaining signal channels, the subset will be chosen in a way so that the global average deviation is minimum.

Some embodiments may be able to forecast the expected error in the resulting estimated map versus a hypothetical fully measured map. For example, interpolation accuracy using the current signal channel subset can be evaluated by applying it to the fit map database and calculating the errors. This would allow the fitting clinician to choose an appropriate balance between a more rapid fitting based on fewer measures with likely lower accuracy versus a more accurate but slower fitting based on a larger number of measures.

Any psychoacoustic or objective measure can be used with the embodiments described above. That means, that if psychoacoustically measured MCL levels across all signal channels are the target of the process, then embodiments of the invention allow for identifying an optimum subset of signal channels based on an analysis of psychoacoustically-based fit maps. If ESRT values across all signal channels are targeted, then embodiments of the invention allow identifying an optimum subset of signal channels based on an analysis of measured ESRT levels across the signal channels. Of course, the quality of the results of specific embodiments depends on proper compilation of the fit map database which the analysis is based on.

Embodiments of the invention also include implantable devices and ear implant systems fit by a method as discussed above. Although various exemplary embodiments of the invention have been disclosed, it should be apparent to those skilled in the art that various changes and modifications can be made which will achieve some of the advantages of the invention without departing from the true scope of the invention. While the foregoing is described in the specific context of a cochlear implant system, it should be understood as broadly applicable to all classes of ear implant systems including all implantable arrangements that provide stimulation signals affecting the hearing and/or balance sensing systems, including without limitation combined electric—acoustic stimulation (EAS) hearing systems, middle ear implants, bone conduction hearing implants, auditory brainstem implants, vestibular implants, and Meniere's implants.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for fitting a multi-channel cochlear implant system to an implanted patient, the method comprising:
   accessing a fit map database containing parameter data from fit maps of previously measured cochlear implant patients;
   establishing for subsets of signal channels in each fit map an average deviation between estimated parameter values and measured parameter values across signal channels not in a given subset based on measured parameter values of signal channels in the given subset;
   identifying for a given number of signal channels a subset of the same number of signal channels having a minimum average deviation;
   measuring fit parameters for signal channels in the identified subset; and
   estimating fit parameters for signal channels not in the identified subset.

2. A method according to claim 1, wherein measuring fit parameters includes using psychoacoustic measurements.

3. A method according to claim 1, wherein measuring fit parameters includes using objective measurements.

4. A method according to claim 1, wherein estimating fit parameters includes using linear interpolation.

5. A method according to claim 1, further comprising:
   increasing the given number of signal channels and repeating the identifying, measuring and estimating steps.

6. A method according to claim 5, wherein the initial given number of signal channels is 1.

7. A method according to claim 5, wherein the increasing step is performed a plurality of times as determined by a clinician fitting the implanted patient.

8. A method according to claim 5, wherein the increasing step is performed a plurality of times as determined by fit software using the method.

9. A method according to claim 1, wherein identifying the subset of signal channels with the minimum average deviation includes identifying an order in which to measure the signal channels in the identified subset.

10. A method according to claim 1, wherein the given number of signal channels is determined by a clinician fitting the implanted patient.

11. A method according to claim 1, wherein the given number of signal channels is determined by fit software using the method.

12. A cochlear implant system fit to an implanted patient using the method according to any of claims 1-11.

13. A computer program product in a non-transitory computer readable storage medium for fitting to an implanted patient a cochlear implant system having a plurality of signal channels, the product comprising:
   program code for accessing a fit map database containing parameter data from fit maps of previously measured cochlear implant patients;
   program code for establishing for subsets of signal channels in each fit map an average deviation between estimated parameter values and measured parameter values across signal channels not in a given subset based on measured parameter values of signal channels in the given subset;
   program code for identifying for a given number of signal channels a subset of the same number of signal channels having a minimum average deviation;
   program code for measuring fit parameters for signal channels in the identified subset; and
   program code for estimating fit parameters for signal channels not in the identified subset.

14. A product according to claim 13, wherein the program code for measuring fit parameters includes program code for using psychoacoustic measurements.

15. A product according to claim 13, wherein the program code for measuring fit parameters includes program code for using objective measurements.

16. A product according to claim 13, wherein the program code for estimating fit parameters includes program code for using linear interpolation.

17. A product according to claim 13, further comprising:
   program code for increasing the given number of signal channels and repeating the identifying, measuring and estimating program code.

18. A product according to claim 17, wherein the initial given number of signal channels is 1.

19. A product according to claim 17, wherein the increasing step is performed a plurality of times as determined by a clinician fitting the implanted patient.

20. A product according to claim 17, wherein the increasing step is performed a plurality of times as determined by fit software using the product.

21. A product according to claim 13, wherein identifying the subset of signal channels with the minimum average deviation includes identifying an order in which to measure the signal channels in the identified subset.

22. A product according to claim 13, wherein the given number of signal channels is determined by a clinician fitting the implanted patient.

23. A product according to claim 13, wherein the given number of signal channels is determined by fit software using the product.

* * * * *